US010292635B2

(12) United States Patent
Griffiths et al.

(10) Patent No.: US 10,292,635 B2
(45) Date of Patent: May 21, 2019

(54) SYSTEM AND METHOD FOR ASSESSING IMPULSE CONTROL DISORDER (71) Applicant: Global Kinetics Corporation Limited, Melbourne (AU)

(72) Inventors: Robert Irwin Griffiths, Melbourne (AU); Malcolm Kenneth Home, Melbourne (AU); Andrew H. Evans, Melbourne (AU)

(73) Assignee: Global Kinetics Pty Ltd, Melbourne (AU)

( * ) Notice: Subject to any disclaimer, the term of this patent is extended or adjusted under 35 U.S.C. 154(b) by 452 days.

(21) Appl. No.: 14/771,965

(22) PCT Filed: Feb. 28, 2014

(86) PCT No.: PCT/AU2014/000191
§ 371 (c)(1),
(2) Date: Sep. 1, 2015

(87) PCT Pub. No.: WO2014/131090
PCT Pub. Date: Sep. 4, 2014

(65) Prior Publication Data
US 2016/0022192 A1    Jan. 28, 2016

(30) Foreign Application Priority Data

Mar. 1, 2013 (AU) ............................... 2013900705
Aug. 9, 2013 (AU) ............................... 2013903014

(51) Int. Cl.
*G16H 50/30* (2018.01)
*A61B 5/16* (2006.01)
(Continued)

(52) U.S. Cl.
CPC .............. *A61B 5/16* (2013.01); *A61B 5/4076* (2013.01); *G06F 19/00* (2013.01);
(Continued)

(58) Field of Classification Search
CPC ........................................................ A61B 5/16
See application file for complete search history.

(56) References Cited

U.S. PATENT DOCUMENTS 4,306,291 A    12/1981   Zilm et al.
4,730,253 A     3/1988   Gordon
(Continued)

FOREIGN PATENT DOCUMENTS

EP    0535508 A1    4/1993
EP    1595497 A1   11/2005
(Continued)

OTHER PUBLICATIONS

Pathophysiology of Involuntary Movements in Parkinson's Disease, Yanagisawa, et al., Euro. Neurol, vol. 26, Suppl 1., © 1987 S. Karger A.G., pp. 30-40.
(Continued)

*Primary Examiner* — John R Downey
(74) *Attorney, Agent, or Firm* — Banner & Witcoff, Ltd.

(57) ABSTRACT

A method of assessing the likelihood that an individual has impulse control disorder. The individual is provided with an actuator, and instructed to actuate the actuator as an acknowledgement of when the individual has completed a reward task. Actuation of the actuator is monitored and recorded. An automated diagnosis of ICD is produced and output, wherein a greater degree of actuation of the actuator by the individual is taken to indicate a greater likelihood that the individual has impulse control disorder.

6 Claims, 6 Drawing Sheets

(51) Int. Cl.
G09B 19/00 (2006.01)
G06F 19/00 (2018.01)
A61B 5/00 (2006.01)

(52) U.S. Cl.
CPC ......... *G06F 19/3456* (2013.01); *G09B 19/00* (2013.01); *G16H 50/30* (2018.01); *A61B 5/4082* (2013.01); *A61B 5/4833* (2013.01); *A61B 5/6887* (2013.01)

(56) References Cited

U.S. PATENT DOCUMENTS

| | | | |
|---|---|---|---|
| 4,771,792 | A | 9/1988 | Seale |
| 4,817,628 | A | 4/1989 | Zealear et al. |
| 4,836,218 | A | 6/1989 | Gay et al. |
| 5,293,879 | A | 3/1994 | Vonk et al. |
| 5,913,310 | A | 6/1999 | Brown et al. |
| 6,053,866 | A | 4/2000 | McLeod et al. |
| 6,561,992 | B1 | 5/2003 | Eberhart et al. |
| 6,878,121 | B2 | 4/2005 | Krausman et al. |
| 7,983,872 | B2 | 7/2011 | Makino et al. |
| 8,187,209 | B1 | 5/2012 | Giuffrida |
| 10,085,689 | B1 | 10/2018 | Giuffrida et al. |
| 2002/0082222 | A1* | 6/2002 | Shapira .............. A61K 31/00 514/23 |
| 2002/0156392 | A1 | 10/2002 | Arai et al. |
| 2004/0087878 | A1 | 5/2004 | Krausman et al. |
| 2004/0220493 | A1 | 11/2004 | Teicher et al. |
| 2005/0075553 | A1 | 4/2005 | Sakai et al. |
| 2005/0234309 | A1 | 10/2005 | Klapper |
| 2005/0240086 | A1 | 10/2005 | Akay |
| 2005/0283096 | A1 | 12/2005 | Chau et al. |
| 2006/0287614 | A1 | 12/2006 | Hogan et al. |
| 2008/0033259 | A1 | 2/2008 | Manto et al. |
| 2008/0045804 | A1 | 2/2008 | Williams |
| 2008/0053253 | A1 | 3/2008 | Moore et al. |
| 2009/0062696 | A1 | 3/2009 | Nathan et al. |
| 2009/0326419 | A1 | 12/2009 | Gonzalez Rojas et al. |
| 2010/0030119 | A1 | 2/2010 | McNames et al. |
| 2011/0098608 | A1 | 4/2011 | Griffiths et al. |
| 2014/0074179 | A1 | 3/2014 | Heldman et al. |
| 2014/0364770 | A1 | 12/2014 | Slonneger et al. |
| 2015/0073310 | A1 | 3/2015 | Pracar et al. |
| 2015/0157274 | A1 | 6/2015 | Ghassemzadeh et al. |

FOREIGN PATENT DOCUMENTS

| | | |
|---|---|---|
| EP | 1714612 A2 | 10/2006 |
| EP | 1994883 A1 | 11/2008 |
| EP | 2660745 A2 | 11/2013 |
| JP | 2004136074 A | 5/2004 |
| JP | 2004261525 A | 9/2004 |
| JP | 2005152053 A | 6/2005 |
| JP | 2007075428 A | 3/2007 |
| WO | 1997039677 A1 | 10/1997 |
| WO | 1999052038 A1 | 10/1999 |
| WO | 2003053245 A2 | 7/2003 |
| WO | 03063876 A2 | 8/2003 |
| WO | 2004008427 A1 | 1/2004 |
| WO | 2004084725 A1 | 10/2004 |
| WO | 2005120347 A1 | 12/2005 |
| WO | 2006088415 A1 | 8/2006 |
| WO | 2006105621 A1 | 10/2006 |
| WO | 2007105648 A1 | 9/2007 |
| WO | 2007136677 A2 | 11/2007 |
| WO | 2008037260 A2 | 4/2008 |
| WO | 2009149520 A1 | 12/2009 |
| WO | 2012129636 A1 | 10/2012 |
| WO | 2013012625 A1 | 1/2013 |
| WO | 2014131090 A1 | 9/2014 |
| WO | 2015118534 A1 | 8/2015 |
| WO | 2015131244 A1 | 9/2015 |

OTHER PUBLICATIONS

Portable System for Quantifying Motor Abnormalities in Parkinson's Disease, Ghika, et al., ISEE Transactions on Biomedical Engineering, vol. 40, No. 3, © 1993 IEEE, pp. 276-283.
Postural and Resting Tremors in Parkinson's Disease, Gresty, et al., Advances in Neurology, vol. 40, © 1984 Raven Press, New York, pp. 361-364.
Quantification of Chorea in Huntington's Disease by Power Spectral Analysis, Weitzman, et al., Diseases of the Nervous System, May 1976, pp. 264-268.
Quantification of tremor with a digitizing tablet, Elble, et al., Journal of Neuroscience Methods, vol. 32, © 1990 Elsevier Science Publishers B.V., pp. 193-198.
Quantitative Assessment of Parkinsonian Patients by Continuous Wrist Activity Monitoring, Van Hilten, et al., Clinical Neuropharmacology, vol. 16, No. 1, © 1993 Raven Presss, Ltd., pp. 36-45.
Relationship between Tardive Dyskinesia, L-Dopa-Induced Hyperkinesia and Parkinsonism, Gerlach, Psychopharmacology vol. 51, © Springer-Verlag 1977, pp. 259-263.
SHIMMER—Sensing Health with Intelligence, Modularity, Mobility, and Experimental Reusability, SHIMMER Hardware Guide Rev. 1.3, dated Oct. 3, 2006 © 2006 Intel Corporation, 15 pages.
Short- and Long-Duration Responses to Levodopa During the First Year of Levodopa Therapy, Nutt et all, Annals of Neurology vol. 42, No. 3, Sep. 1997, © 1997 by the Ameircan Neurological Association, pp. 349-355.
Slowness of Movement in Parkinson's Disease, Marsden, Movement Disorders, vol. 1. Suppl. 1, © 1989 Movement Disorder Society, pp. S26-S37.
Spectral analysis of tremor: understanding the results, Gresty, et al., Journal of Neurology, Neurosurgery, and Psychiatry, vol. 53, 1990, pp. 976-981.
The accuracy and precision of timing of self-paced, repetitive movements in subjects with Parkinson's disease, O'Boyle, et al., Brain 1996, vol. 119, © 1996 Oxford University Press pp. 51-70.
The measurement of tremor using simple laser systems, Beuter, et al., Journal of Neuroscience Methods vol. 53 © 1994 Elsevier Science B.V., pp. 47-54.
The Relation Between EMG Activity and Kinematic Parameters Strongly Supports a Role of the Action Tremor in Parkinsonian Bradykinesia, Carboncini, et al., Movement Disorders vol. 16, No. 1, © 2001 Movement Disorder Society, pp. 47-57.
The Unified Parkinson's Disease Rating Scale (UPDRS): Status and Recommendations, Movement Disorder Society Task Force on Rating Scales for Parkinson's Disease, Goetz et al., Movement Disorders, vol. 18, No. 7, 2003, pp. 738-750.
Towards a New Method for Kinematic Quantification of Bradykinesia in Patients With Parkinson's Disease Using Triaxial Accelometry, Veltink, et al., 1995 IEEE-EMBC and CMBEC, Theme 5: Neuromuscular Systems/Biomechanics, © IEEE, pp. 1303-1304.
Tremorwatch®, Ref RC/SB Issue date Mar. 30, 2007 © Cambridge Neurotechnology 2007, 2 pages.
Unified Parkinson's Disease Rating Scale Motor Examination: Are Ratings of Nurses, Residents in Neurology, and Movement Disorders Specialists Interchangeable?, Post et al., Movement Disorders Fol. 20, No. 12, © 2005 Movement Disorder Society, pp. 157-1584.
Utility of an Objective Dyskinesia Rating Scale for Parkinson's Disease: Inter- and Intrarater Reliability Asessment, Goetz et al, Movement Disorders vol. 9, No. 4, © 1994 Movement Disorder Society, pp. 390-394.
Validity of Long-Term Electromyography in the Quanitfication of Tremor, Spieker, et al., Movement Disorders, vol. 12., No. 6, © 1997 Movement Disorders Society, pp. 985-991.
Veltink, P. H. et al., "Towards a New Method for Kinematic Quantification of Bradykinesia in Pateints with Parkinson's Disease using Triaxial Accelerometry", IEEE 17th Annual Conference montreal, Quebec, Canada, Engineering in Medician and Biology Society, Sep. 20, 1995, pp. 21303-1304, ISBN: 978-0-7803-2475-6.
Wearable Wireless Sensor Network to Assess Clinical Status in Patients with Neurological Disorders, Lorincz, et al., IPSN '07, Apr. 25-27, 2007, pp. 563-564.
Zwartjes, Daphne G.M. et al., "Ambulatory Monitoring of Activities and Motor Symptoms in Parkinson's Disease", IEEE Transac- (56) References Cited

OTHER PUBLICATIONS tions on Biomedical Engineering, vol. 57, No. 11, IEEE Service Center, Piscataway, NJ, Nov. 1, 2010, pp. 2778-2786, XP011327061, ISSN: 0018-9294, doi: 10.1109/TBME.2010.2049573.
Extended European Search Report for European Application No. 14756592.3, Search completed Sep. 9, 2016, dated Sep. 16, 2016, 11 Pgs.
International Search Report and Written Opinion for International Application PCT/AU2014/000191, report completed on Mar. 27, 2014, dated Mar. 27, 2014, 22 pgs.
Chamberlain et al, Samuel, "Motor Inhibition and Cognitive Flexibility in Obsessive-Compulsive Disorder and Trichotillomania", American Journal of Psychiatry, vol. 163. No. 7, Jul. 1, 2006 (Jul. 1, 2006), pp. 1282-1284.
Dong et al., Gaungheng, "Impulse inhibition in people with Internet. addiction disorder: Electrophysiological evidence from a Go/NoGo study", Neuroscience Letters, Limerick, IE. vol. 485, No. 2, Nov. 19, 2010 (Nov. 19, 2010), pp. 138-142.
Grant et al., Joh, "Cognitive dysfunction in childhood-onset pathologic skin.picking", Journal of Obsessive-Compulsive and Related Disorders, vol. 1, No. 2, Jan. 31, 2012 (Jan. 31, 2012), pp. 73-76.
May 5, 2015—(PCT) International Search Report—App. PCT/AU2015/050084.
Nov. 15, 2017—(EP) Extended Search Report—App. 12758333.7.
A comparison of neuropsychological effects of thalamotomy and thalamic stimulation, Schuurman, et al., Neurology © 2002, vol. 59, pp. 1232-1239.
A New Actigraph for Long-Term Registration of the Duration and Intesity of Tremor ande Movement, van Someren, et al., IEEE Transactions on Biomedical Engineering, vol. 45, No. 3, Mar. 1998, pp. 386-395.
A new approach in the assessment of motor activity in Parkinson's disease, van Hilten et al., Journal of Neurology, Neurosurgery, and Psychiatry 1991; 54, pp. 976-979.
A Normative Study of Postural Tremor of the Hand, Wade et al., Arch. Neurol., vol. 39, Jun. 1982, pp. 358-362.
A quantitative study of levodopa-induced dyskinesia in Parkinson's disease, Caligiuri et al., Journal of Neural Transmission [P-D Sect] 1993, vol. 6, © Springer-Verlag 1993, pp. 89-98.
Accelerometric Assessment of Tardive Dyskinesia, Tryon, et al., Am. J. Psychiatry, 1987, vol. 14, No. 12, pp. 1584-1587.
Accuracy of clinical diagnosis of idiopathic Parkinson's disease: a clinico-pathological study of 100 cases, Hughes et al., Journal of Neurology, Neurosurgery, and Psychiatry 1992 55: pp. 181-184.
Actigraphic Monitoring of Movement and Rest-Activity Rhythms in Aging, Alzheimer's Disease, and Parkinson's Disease, Van Someren, IEEE Transactions on Rehabilitation Engineering, vol. 5, No. 4, Dec. 1997, pp. 394-398.
Advanced Analysis of Wearable Sensor Data to Adjust Medication Intake in Patients with Parkinson's Disease, Sherrill, at al., Proceedings of the 2nd International IEEE EMBS Conference on Neural Engineering, Mar. 2005, © 2005 IEEE, pp. v-viii.
Ambulatory accelerometry in Parkinson's disease, Hoff, University of Leiden (Doctoral Thesis), Sep. 30, 2005, 107 pages.
Ambulatory monitoring of tremor and other movements before and aftger thalamotomy: a new quantitative technique, van Someren, et al., Journal of the Neurological Sciences, vol. 117, © 1993 Elsevier Science Publishers, pp. 16-23.
An ambulatory dyskinesia monitor, Manson et al., J. Neurol. Neurosurg. Psychiatry, vol. 68, 2000, pp. 196-201.
An Ambulatory System to Quanitfy Bradykinesia and Tremor in Parkinson's Disease, Salarian, et al., Proc. of the 4th Annual IEEE Conf on Information Technology Applications in Biomedicine, UK, © 2003 IEEE, pp. 35-38.
Application EMGs spectral analysis method for the objective diagnosis of different clinical forms of Parkinson's disease, Andreeva, et al., Electromyogr.clin.Neurophysiol., 1996, vol. 36, pp. 187-192.
Assessment of Extrapyramidal Disorders, Marsden et al., Br. J. clin.Pharmac, vol. 11, © Macmillan Publishers Ltd. 1981, pp. 129-151.

Assessment of Rest Tremor in Parkinson's Disease, Cleeves, et al, Advances in Neurology, vol. 45, Raven Press, New York © 1985, pp. 349-352.
Assessment of symptoms of Parkinson's disease by appartive methods, Kraus. et al., J. Neural Transm (1987) [Suppl] vol. 25: pp. 89-96.
Automatic Assessment of Levodopa-Induced Dyskinesias in Daily Life by Neural Networks, Noël L.W. Kleijsers, MSc, et al., Movement Disorders, vol. 18, No. 1, 2003, © 2002 Movement Disorder Society, pp. 70-80.
Bradykinesia and hypokenisia in Parkinson's disease: what's in a name?, van Hilten, et al., J. Neural Transm, vol. 105, © Springer-Verlag 1998, pp. 229-237.
Bradykinesia in Parkinson's Disease: Disorders of Onset and Execution of Fast Movement, Yanagisawa, et al., Eur Neurol 1989, vol. 29, Suppl. 1, © 1989 S. Karger AG, pp. 19-28.
Characteristics of Handwriting of Patients with Huntington's Disease, Phillips, et al., Movement Disorders vol. 9, No. 5, 1994, pp. 521-530.
Clinical Neurophysiological Assessment of Parkinson's Disease, Gonce et al., Advances in Neurology, vol. 40, © 1984 Raven Press, New York, pp. 365-373.
Computational Analysisof Open Loop Handwriting Movements in Parkinson's Disease: A Rapid Method to Detect Dopamimetic Effects, Eichhorn, et al., Movement Disorders vol. 11, No. 3, 1996, pp. 289-297.
Defining Parkinson's Disease and Parkinsonism, Rajesh Pahwa et al, Etiology of Parkinson's Disease, 1995, pp. 1-54.
Disability profiles and objective quantitative assessment in Parkinson's disease, Johnels et al., Acta Neurol. Scand., vol. 79, 1989, pp. 227-238.
Dunnewold, R.J. W et al., "Quantitative Assessment of Bradykinesia in Patients with Parkinson's Disease", Journal of Neuroscience Methods, Elsevier Science Publisher B.V., Jun. 6, 1997, vol. 74, No. 1, pp. 107-112.
Evans, Andrew H. et al., "A Conditioned Response as a Measure of Impulsive-Compulsive Behaviours in Parkinson's Disease", PLoS ONE, vol. 9, No. 2, Feb. 24, 2014, p. e89319, XP055300236, doi:10.1371/journal.pone.0089319.
Gravitational artifact in accelerometric measurements of tremor, Elble, Clinical Neurophysiology, vol. 116, © 2005 Internation Federation of Clinical Neurophysiology, pp. 1638-1643.
Griffiths, Robert I., "Automated Assessment of Bradykinesia and Dyskinesia in Parkinson's Disease", Journal of Parkinson's Disease, vol. 2, No. 1, Jan. 1, 2012, pp. 47-55, XP055300735, doi: 10.3233/JPD-2012-11071.
Induction of Chorea and Dystonia in Parkinsonian Primates, Boyce et al., Movement Disorders vol. 5, No. 1, ©1990 Movement Disorder Society, pp. 3-7.
Instrumental Assessment of Lingual Motor Instability in Tardive Dyskisia, Caligiuri, et al., Neuropsychopharmacology, vol. 2, No. 4, 1989, pp. 309-312.
Is Parkinsonian Arm Tremor a Resting Tremor?, Hadar, et al., Eur Neurol 1993, vol. 33, pp. 221-228.
Kinesia Movement Disorders Assessment System, Wireless Gyroscope, Wireless Accelerometer, http://www.clevemed.com/Kinesia/hardware.shtml, retrieved Aug. 4, 2011, 2 pages.
Levodopa-induced dyskinesia: Review, observations, and speculations, Nutt, Neurology, 1990, vol. 40, pp. 340-345.
Levodopa-Induced Dyskinesias in Parkinson's Disease Phenomenology and Pathophysiology, Marconi, et al., Movement Disorders, vol. 9, No. 1, 1994, pp. 2-12.
Long-term monitoring of gait in Parkinson's disease, Moore, et al., Gait & Posture vol. 26, 2007, pp. 200-207.
Motor complications associated with chronic levodopa therapy in Parkinson's disease, Obeso,et al., Neurology vol. 38, Suppl 2, Nov. 1989, pp. 11-19.
Motor Response to Levodopa and the Evolution of Motor Fluctuations in the First Decade of Treatment of Parkinson's Disease, McColl, et al., Movement Disorders vol. 17, No. 6, © 2002 Movement Disorder Society, pp. 1227-1234.

(56) References Cited

OTHER PUBLICATIONS

Motor response to levodopa in patients with parkinsonian motor fluctuations: a follow-up study over three years, Hughes, et al., Journal of Neurology, Neurosurgery, and Psychiatry, vol. 57, 1994, pp. 430-434.
Movement Disorder Society-Sponsored Revision of the Unified Parkinson's Disease Rating Scale (MDS-UPDRS): Scale Presentation and Clinimetric Testing Results, Goetz et al, Movement Disorders vol. 23, No. 15, © 2008 Movement Disorder Society, pp. 2129-2170.
Movement Variability and Bradykinesia in Parkinson's Disease, Sheridan, et al., Brain 1990, vol. 113, © Oxford University Press 1990, pp. 1149-1161.
New Actigraph for Long-Term Tremor Recording, Van Someren et al., Movement Disorders, vol. 21, No. 8, 2006, pp. 1136-1143.
Observations on the design and specification of a wrist-worn human activity monitoring system, Redmond, et al., Behavior Research Methods, Instruments, and Computers, 1985, vol. 17, No. 6, pp. 659-669.
On the Structure of Motor Symptoms of Parkinson's Disease, Stochl, et al., Movement Disorders vol. 23, No. 9, 2008, pp. 1307-1315.
Online Monitoring of Dyskinesia in Patients with Parkinson's Disease; Utilizing Wearable Movement Sensors to Successfully Detect and Assess Severity of Parkinsonian Symptoms in Daily Life, Keijsers et al., IEEE Engineering in Medicine and Biology Magazine, May/Jun. 2003, pp. 96-103.
Patel, Shyamal et al., "Monitoring Motor Fluctuations in Patients with Parkinson's Disease using Wearable Sensors", IEEE Transactions on Information Technology in Biomedicine, Nov. 1, 2009, vol. 13, No. 6, pp. 864-873.
Patel, Shyamal et al., "Using Wearable Sensors to Enhance DBS Parameter Adjustment for Parkinson's Disease Patients through Measures of Motor Response", Proceedings of the 3rd IEEE-EMBS International Summer School and Symposium on Medical Devices and Biosensors, Sep. 1, 2006, pp. 141-144, ISBN: 978-0-7803-9786-6.
Patel, Shyamal, "Using Wearable Sensors to Predict the Severity of Symptoms and Motor Complications in late stage Parkinson's Disease", 30th Annual International IEEE EMBS Conference, Engineering in Medicine and Biology Society, Aug. 20, 2008, Piscataway, NJ, pp. 3686-3689.
Aug. 1, 2013—(US) Maglione et al., Actigraphy for the Assessment of Sleep Measures in Parkinson's Disease, pp. 1209-1217, https://doi.org/10.5665/s1eep.2888.
Aug. 19, 2014—(US) Pan et al., Quantitative Evaluation of the Use of Actigraphy for Neurological and Psychiatric Disorders Behaviioural Neurology, vol. 2014, http://dx.doi.org/10.1155/2014/897282.
2016 vol. 53, No. 4 (US) Bhidayasiri et al., Capturing Nighttime Symptoms in Parkinson Disease: Technical Development and Experimental Verification of Inertial Sensors for Nocturnal Hypokinesia, http://dx.doi.org/10.1682/JRRD.2015.04.0062.
Apr. 21, 2017—(AU) Search Report—App. No. 2016902203.
Aug. 9, 2017—(WO) International Search Report and Written Opinion—App. No. PCT/AU2017/050555.
Mar. 31, 2017—(EP) International Search Report—App. No. PCT/AU2017/050015.
Nov. 25, 2013—(AU) Search Report (International-type)—App. 2013903014.
Sep. 1, 2015—(WO) International Preliminary Report on Patentability—App. PCT/AU2014/000191.
Jun. 30, 2017—(AU) Examination Report—App. 2014223313.
Aug. 9, 2018—(IN) Examination Report—App. 211/CHENP/2011.
Aug. 27, 2018—(US) Office Action—U.S. Appl. No. 15/123,568.
Perlmutter, Joel S. And Mink, Jonathan W., "Deep Brain Stimulation", Annual Review of Neuroscience, vol. 29, No. 1, 2006, pp. 2229-257, dor 10.1146/annurev.nuero.29.051605.112824.

\* cited by examiner

SYSTEM AND METHOD FOR ASSESSING IMPULSE CONTROL DISORDER

CROSS-REFERENCE TO RELATED APPLICATIONS

This application claims the benefit of Australian Provisional Patent Application No. 2013900705 filed 1 Mar. 2013, which is incorporated herein by reference, and also claims the benefit of Australian Provisional Patent Application No. 2013903014 filed 9 Aug. 2013, which is incorporated herein by reference.

TECHNICAL FIELD

The present invention relates to a system and method for remotely monitoring individual behaviour, and in particular to a system and method configured to isolate ICD-like behaviour and remotely monitor ICD-like behaviour.

BACKGROUND OF THE INVENTION

Impulse control disorder, or ICD, is a class of psychiatric disorders characterized by impulsivity, namely the failure to resist a temptation, urge or impulse. ICD involves pathological behaviour (impulsive-compulsive behaviours (ICBs)) which can include one or more of impulsive gambling, impulsive eating, impulsive buying, impulsive sexual behaviour, impulsive cleaning, Internet addiction, punding, hobbyism, hoarding, kleptomania, impulsive smoking, impulsive medication use, and/or one or more of a large number of other impulsive behaviours.

Dopamine agonists used for the treatment of Parkinson's disease (PD) are known to cause impulse control disorder, amongst other causes.

Diagnosing ICD can be difficult due to the secretiveness of many of the behaviours, and/or due to the need for the individual to self-report the existence and/or severity of the behaviour. Presently, ICD behaviour is evaluated in the clinical environment, requiring highly trained and astute professionals, and ICD diagnosis and treatment is thus relatively expensive. Clinical evaluation of ICD nevertheless can be imprecise as the individual's inhibitions in the clinical environment may motivate the individual to mask symptoms, and also because the clinician often relies on subjective self-reporting and patients often fail to report ICBs due to embarrassment and/or a lack of awareness of the relationship between PD and ICD.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method of assessing the likelihood that an individual has impulse control disorder, the method comprising:

providing the individual with an actuator, and instructing the individual to actuate the actuator as an acknowledgement of when the individual has completed a reward task;

monitoring and recording the actuation of the actuator;

producing an automated diagnosis of ICD, wherein a greater degree of actuation of the actuator by the individual is taken to indicate a greater likelihood that the individual has impulse control disorder; and outputting the automated diagnosis of whether the individual has impulse control disorder.

According to another aspect the present invention provides a non-transitory computer readable medium for assessing the likelihood that an individual has impulse control disorder, comprising instructions which when executed by one or more processors causes performance of the following:

processing records of actuation of an actuator by an individual, the individual having been instructed to actuate the actuator as an acknowledgement of when the individual has completed a reward task;

producing an automated diagnosis of ICD, wherein a greater degree of actuation of the actuator by the individual is taken to indicate a greater likelihood that the individual has impulse control disorder; and outputting the automated diagnosis of whether the individual has impulse control disorder.

According to another aspect the present invention provides a computer program product comprising computer program code means to make a computer execute a procedure for assessing the likelihood that an individual has impulse control disorder, the computer program product comprising computer program code means for carrying out the method of the first aspect.

In some embodiments of the invention, the task of actuating the actuator is made salient to the reward task from the perspective of the individual. An individual having ICD is more likely to display ICD-like behaviour by repetitively actuating the actuator if the actuator is considered salient to the reward task. The reward task may be pleasurable; favourable or desirable to the individual. Notably, the present invention does not require that the performance of the task itself is monitored; rather, the diagnostic configuration provided by the present invention provides for a separate actuator which the individual is motivated to actuate as an acknowledgement of completion of the reward task. Such embodiments of the present invention then monitor for the presence or absence of ICD-like behaviour in relation to the actuator, but not necessarily in relation to the reward task.

Assessment of a degree of actuation of the actuator is in some embodiments made by comparison to an expected degree of actuation of the actuator. For example, the user might be instructed or expected to actuate the actuator once upon completion of a reward task, whereby actuation of the actuator more than once is taken to indicate a greater likelihood that the individual has impulse control disorder. For example, in some embodiments if the user actuates the actuator moderately more than expected, such as by a number of times which is more than 40% more than the expected degree of actuation, an output may be generated to indicate that the user is at risk of ICD. In some embodiments if the user actuates the actuator significantly more than expected, such as by a number of times which is more than 65% more than the expected degree of actuation, an output may be generated to indicate that the user has ICD. Thus, in monitoring for a greater degree of actuation of the actuator, some embodiments may monitor for actuation of the actuator beyond what is required or has been instructed in order to complete the reward task.

The actuator may be a button, dial, lever, questionnaire tick-box, or any sensor or input device responsive to a motor response of the individual. For example the actuator may be a button of a device which reminds the individual to take medication, wherein the device is configured to remind the individual to take medication when required, and wherein pressing the button once deactivates the reminder to indicate that the medication has been taken. A user pressing the button more than once can then be taken as indicating a greater likelihood that the individual has impulse control disorder. The device may be body-worn such as a wrist-worn alarm device, or may be located separately to the individual such as a smart phone, tablet device or personal computer configured to generate reminders to the individual.

Preferably, the individual is given the impression that the actuator is for an alternative purpose and is not informed that their actuation of the actuator is being monitored beyond that alternative purpose. In such a state of mind any ICD-like behaviour of the individual is more likely to manifest in an uninhibited manner in relation to the actuator, and to be realised as an impulsive actuation pattern which can be monitored in a less inhibited, more automated and less costly manner than is provided by clinical evaluation. Moreover, a person suffering ICD is less likely to take excessive medication as a result of having ICD, for example, but in contrast is likely to actuate an actuator many times without reason particularly if the actuator is presented as being salient to the task of taking medication.

Notably, the present invention thus provides for the measurement of impulse behaviour in PD by monitoring user activity on device controls which provide other functions. This avoids the need for a patient to self-report ICD behaviour nor undertake a self-assessment, and thus avoids the inaccuracy of such reporting and self-assessment.

This automated system may in some embodiments give the chance to see an ICD risk as it develops, and possibly before conventional ICD behaviour actually occurs.

Upon generation of an indication that a user has ICD or is at risk of ICD, some embodiments may in turn provide for an intervention or therapy to be applied. For example an alert for a medical practitioner may be output to prompt the practitioner to adjust existing dosages of medicines and/or to prescribe and/or administer new medicines or therapies.

BRIEF DESCRIPTION OF THE DRAWINGS

An example of the invention will now be described with reference to the accompanying drawings, in which:

FIG. 6a is a sample output from one day of wrist-worn data logger recording for a patient with low Response Ratio, while FIG. 6c is a sample output from one day of wrist-worn data logger recording for a patient with high Response Ratio.

DESCRIPTION OF THE PREFERRED EMBODIMENTS

EXAMPLE 1

Figure 1:
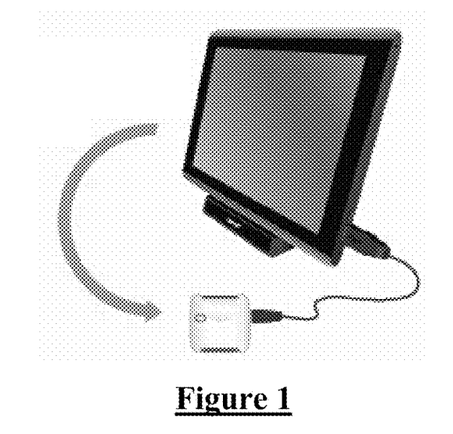
FIG. 1 illustrates configuration of a wrist-worn device with a reminder schedule to assist a patient to take their medication.

The Parkinson's Kinetigraph (PKG) of Global Kinetics Corporation Pty Ltd was used to provide a remote monitoring system and user actuator. Each patient was provided with a wrist-worn data logger. Each wrist-worn data logger was programmed to remind the respective patient when to take their levodopa medication (FIG. 1).

Figure 2:
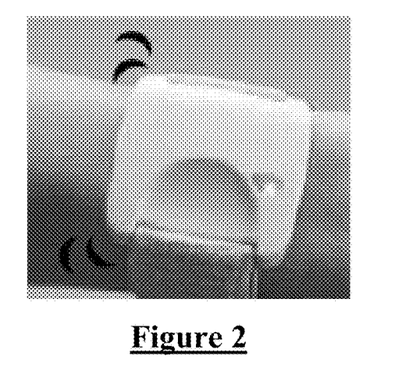
FIG. 2 illustrates generation of an alarm reminding the patient to take a dose of medication.

When it is time for the patient to take their levodopa medication, the wrist-worn data logger will vibrate and a light will flash for 10 seconds (FIG. 2).

Figure 3:
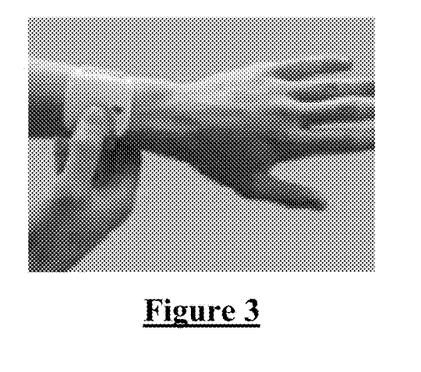
FIG. 3 illustrates the patient actuating a button of the wrist-worn device to indicate that the medication has been taken and to deactivate the alarm reminder.

The individual was instructed that, once they had taken the prescribed medication, they should press the button on the wrist-worn device to deactivate the reminder. The wrist-worn data logger continues to remind the patient to take their medication until they have confirmed that you have done so, by pressing the button (FIG. 3). User confirmation is effected by the user holding their thumb in the thumb groove on the top of the wrist-worn data logger for three seconds, at which time the light will come on. The user then needs to promptly remove their thumb immediately after the light comes on, because, if the user's thumb holds the thumb groove for more than 5 seconds the light will extinguish and the wrist-worn data logger will not deactivate the reminder nor record the time at which the medication was taken. Thus, actuation of the button is unlikely to occur without intent. The three second period and five second period can in other embodiments be reconfigured to any other suitable time.

The wrist-worn data logger records the number of times the button is actuated by the user.

TABLE 1

| | ICD clinical assessment | | | | | response | | | |
|---|---|---|---|---|---|---|---|---|---|
| Patient | Current | Anytime | Hobbys punding etc | Score | ACE | UPDRS III | Expected | Total | % Index | % tile rank |
| A | None | None | None | 0 | 87 | 15 | 50 | 51 | 102 | 27.7 |
| B | None | None | None | 0 | 96 | 7 | 50 | 63 | 126 | 66.6 |
| C | None | Buying | Cleaning (not current) | 3 | 89 | 16 | 40 | 49 | 123 | 60.7 |
| D | None | None | Painting | 1 | 91 | 14 | 20 | 34 | 170 | 90.2 |
| E | None | Sex | None | 2 | 94 | 18 | 60 | 55 | 92 | 15.7 |
| F | Eating | Eating Buying | Internet chat | 6 | 94 | 33 | 70 | 97 | 139 | 75.2 |
| G | Gambling | Gambling | None | 5 | 90 | 29 | 70 | 103 | 147 | 81.8 |
| H | Eating (sometimes) | Eating | Computer | 6 | 91 | 26 | 50 | 186 | 372 | 99 |
| I | Gambling/ Sex | Gambling/ Sex Buying | None | 5 | 87 | 9 | 60 | 110 | 183 | 91.2 |
| J | Gambling Buying | Gambling Buying | Sewing | 6 | 98 | 23 | 70 | 243 | 347 | 98.8 |
| K | Gambling Buying | None | None | 5 | 93 | 15 | 40 | 145 | 363 | 99 |

Eleven patients, denoted "A" to "K" in the first column of Table 1, were clinically interviewed to populate the $2^{nd}$ to $4^{th}$ columns of Table 1. The patients self-reported whether they were currently experiencing ICD behaviour ($2^{nd}$ column), whether they had in the past experienced ICD behaviour ($3^{rd}$ column), or whether they had any current hobbies or punding behaviour ($4^{th}$ column) To produce the $5^{th}$ column ("Score"), the existence of a current ICD behaviour in Column 2 attracted a score of 3, the existence of an ICD behaviour at any time in the past in column 3 was scored as a 2, while the existence of any hobbies or punding in the $4^{th}$ column was scored as a 1. These scores were summed to provide the ICD score in the $5^{th}$ column of Table 5.

Each patient was clinically rated using the Addenbrookes Cognitive Examination, as indicated in the $6^{th}$ column of Table 1, to screen for dementia.

The 7th column of Table 1 shows the clinically determined Unified Parkinson's Disease Rating Scale (UPDRS) score for each patient (Part III, motor examination).

The $8^{th}$ column of Table 1 shows the expected number of responses from each patient via the wrist-worn data logger. This corresponds to the number of occasions upon which the patient was instructed to take medication during the monitored period. For example, patient A's prescription required that the patient take 50 doses of L-dopa during the monitored period, and so the patient was expected to press the button once on each occasion in order to deactivate the reminder and to indicate that that particular dose of medication had indeed been taken.

The $9^{th}$ column of Table 1 shows the actual total number of times that each individual pressed the button during the monitored period. The $10^{th}$ column of Table 1 shows the ratio of the $9^{th}$ column to the $8^{th}$ column, expressed as a percentage. In the $10^{th}$ column, a percentage of about 100 is consistent with no ICD-like behaviour, as this corresponds to the user pressing the button once for each instance of medication, as they have been instructed to do. A percentage greatly exceeding 100 is consistent with ICD behaviour, as the user has been given no reason to press the button more than once for each dose of medication. Most persons not having ICD display a % Index of less than about 140%.

Figure 4A:
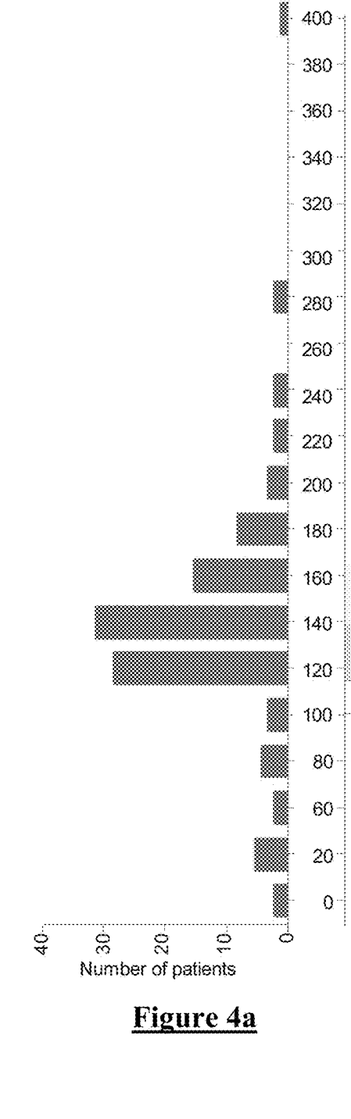
FIG. 4a illustrates a typical distribution of impulsive behaviour of a sample of 109 individuals.

The 11th (right-most) column of Table 1 provides a percentile rank indicating where that patient fits within a reference distribution of patients. The reference distribution was obtained from 109 Parkinson's disease subjects who were not known to have ICD, and who were clinically assessed to obtain the reference distribution, shown in FIG. 1a. In the reference distribution the percentiles are as follows: 50th=114; 75th=138.75; 90th=166.65; 95th=209.25; 99th=364.86. An alternative reference distribution may be suitable in other embodiments.

Figure 4B:
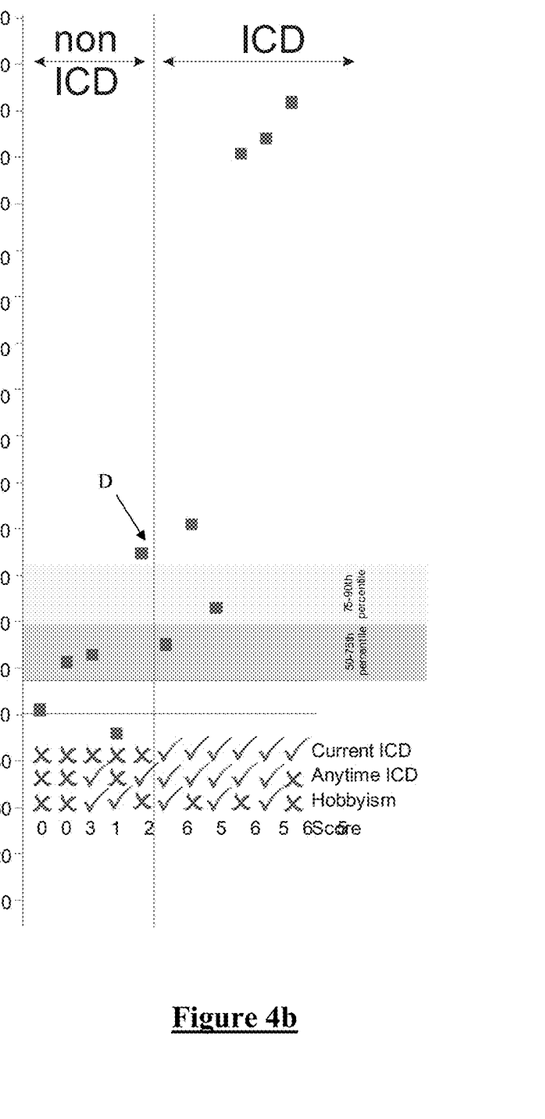
FIG. 4b illustrates the distribution of a study group of 11 persons and the discrimination of ICD made possible by the present invention.
Figure 5:
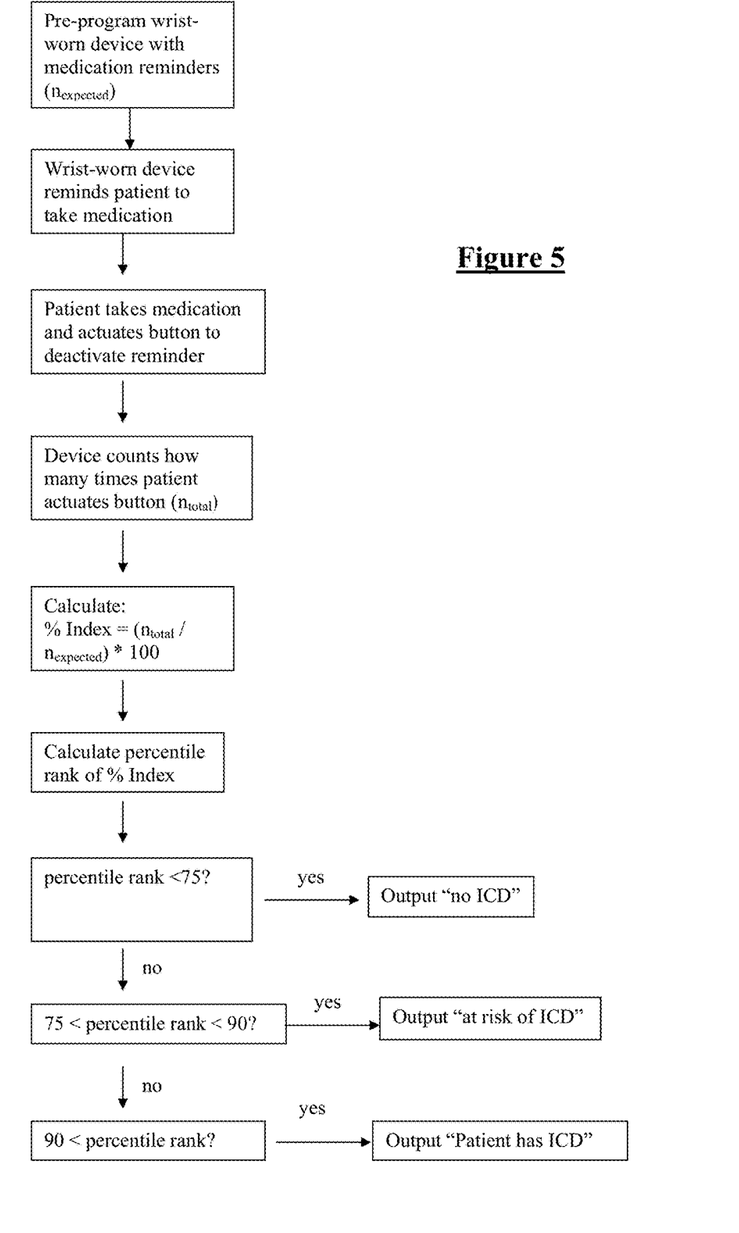
FIG. 5 is a flowchart illustrating the process of one described embodiment of the invention.

The results shown in Table 1 were statistically assessed using a Fishers exact and comparing the number of patients above the 75th percentile with an ICD score greater than 3 (i.e. 4 or above). This returned a statistical p-value of 0.08, providing a good indication that monitoring the individual's actuation behaviour in relation to a reward gives some ability to diagnose ICD. This p-value is particularly encouraging given the small sample size (n=11) of the study shown in Table 1, and larger studies are expected to improve the statistical strength of the merits of the described technique. Additionally from clinical experience of Patient "D" it is believed that this patient may have under-reported past and present ICD behaviours, which may help to explain this outlier point in FIG. 4b. Apart from patient D, FIG. 4b shows that all patients clinically assessed as currently having ICD are correctly diagnosed by the automated technique of the present invention as either "at risk" of ICD ($75^{th}$-$90^{th}$ HU percentile) or "highly likely" to have ICD (above $90^{th}$ percentile). Moreover, using Receiver Operator Curves and comparing ICD Score ($5^{th}$ column of Table 1) to percentile rank ($11^{th}$ column of Table 1) gives a p<0.0001.

Accordingly, the described technique enables an automated diagnostic to be provided. Where the percentile rank ($11^{th}$ column of Table 1) is between the $50^{th}$ and $75^{th}$ percentile, (i.e when the individual's percentage response index ($10^{th}$ column of Table 1) is between 114% and 139%), the individual may be given an automated diagnosis of being "at risk" of ICD. This can be used to alert a clinician to the possibility that the individual has or is developing ICD, potentially at an early stage of the disorder before strong symptoms arise. Moreover, where the percentile rank ($11^{th}$ column of Table 1) is above the $75^{th}$ percentile, (i.e when the individual's percentage response index ($10^{th}$ column of Table 1) is above 139%), the individual may be given an automated diagnosis of "likely having" ICD. Notably, the described technique thus permits monitored users to be diagnosed as "not having", being "at risk", or "likely having" ICD, with good statistical accuracy, and without the need for expensive and subjective clinical appointments.

EXAMPLE 2

Figure 6A:
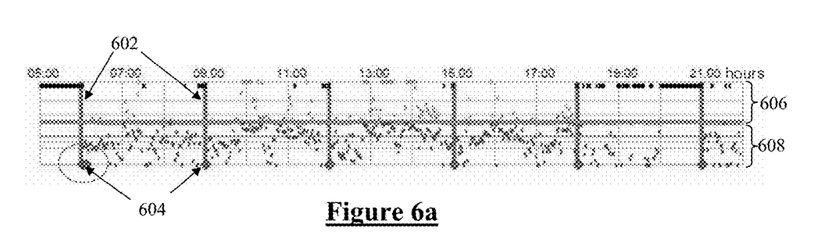

The Parkinson's Kinetigraph (PKG) of Global Kinetics Corporation Pty Ltd was used to provide a remote monitoring system and user actuator, in a similar manner as described for Example 1 above in relation to FIGS. 1 to 3. Additionally, if at times other than the pre-programmed medication times the subject places their thumb on the wrist-worn data logger for 3 seconds, this triggers a brief (1 s) vibration and is recorded as a "redundant response". The timing of both correct responses associated with a reminder, and redundant responses not associated with a reminder, was recorded.

dyskinesia and bradykinesia (respectively) score, which was calculated every 2 minutes, with greater severity of each symptom being represented by increasing distance from the middle of the graph. The horizontal lines indicate the respective median, $75^{th}$ percentile and $90^{th}$ percentile of controls. The vertical lines 602 indicate the times at which medications were prescribed, and the diamonds 604 represent when the taking of medication was acknowledged by the patient. This patient reflected in FIG. 6a provided a second acknowledgment to the 6:00 am dose, shortly after the first acknowledgement (circled), thus providing 7 acknowledgments for 6 doses. The response ratio (RR) for this patient was thus 116% (100×7/6).

As expected, each reminder (indicated by vertical bars 602) is closely followed by a respective acknowledgment from the user (diamond markers 604). This subject received six reminders in the day shown, and gave seven acknowledgements, one acknowledgement per reminder with the

TABLE 2

| Percentile | Age | Durat'n | LED | UPDRS 1 | UPDRS 2 | UPDRS 3 | UPDRS 4 | UPDRS Total | ACE-R | SCOPA-COG | BDI | BIS/BAS | STAI | AS |
|---|---|---|---|---|---|---|---|---|---|---|---|---|---|---|
| Low RR | | | | | | | | | | | | | | |
| $25^{th}$ | 51 | 6 | 525 | 0 | 6 | 7 | 2 | 17 | 91 | 26 | 6 | 66 | 53 | 5 |
| $50^{th}$ | 73 | 10 | 728 | 2 | 8 | 14 | 4 | 33 | 96 | 28 | 7 | 70 | 63 | 7 |
| $75^{th}$ | 76 | 14 | 1000 | 3 | 13 | 23 | 7 | 40 | 97 | 32 | 10 | 77 | 86 | 11 |
| High RR | | | | | | | | | | | | | | |
| $25^{th}$ | 64 | 14 | 654 | 1 | 11 | 9 | 6 | 33 | 86 | 23 | 8 | 73 | 60 | 3 |
| $50^{th}$ | 69 | 16 | 1207 | 3 | 12 | 19 | 8 | 44 | 91 | 30 | 15 | 77 | 77 | 7 |
| $75^{th}$ | 75 | 22 | 2100 | 5 | 17 | 28 | 10 | 53 | 95 | 32 | 21 | 79 | 105 | 17 |
| False Neg | | | | | | | | | | | | | | |
| $25^{th}$ | 61 | 5 | 682 | 1 | 13 | 14 | 3 | 32 | 84 | 22 | 8 | 63 | 78 | 8 |
| $50^{th}$ | 64 | 9 | 1090 | 2 | 14 | 18 | 6 | 39 | 94 | 29 | 10 | 72 | 82 | 11 |
| $75^{th}$ | 75 | 13 | 1791 | 4 | 20 | 40 | 8 | 73 | 94 | 35 | 13 | 79 | 98 | 14 |

To obtain the data shown in Table 2, a blinded examiner administered the Starkstein Apathy scale and the Questionnaire for Impulsive-Compulsive Disorders in Parkinson's disease (QUIP). QUIP scoring was made into a numerical scale by scoring Category A as six, Category B as five and Category C as four if they were current and as three, two and one respectively if they were some time in the past. The United Parkinsons Disease Rating Scale (parts 1-4), the SCOPA Cog, the Addenbrooke's Cognitive Assessment—Revised (Australian Version) were all performed in the "on" state. Anti-Parkinson's Medications including the total levodopa equivalent dose (LED) and dopamine 2 receptor agonist use, age and age of onset of disease were all recorded. Further, patients were instructed to complete the Beck Depression Inventory (BDI), BIS/BAS (Behavioural Inhibition Scale/Behavioural Activation Scale) and State Trait Anxiety Inventory (STAT) in isolation. The BDI was used to assess whether the subject suffers from depression and the STAI used to indicate the presence of state and/or trait anxiety. The BIS/BAS questionnaire was scored using the BIS/BAS scale (reverse scoring apart from questions 2 and 22) and the total score was split into four parts; BIS, BAS drive, BAS fun seeking and BAS reward responsiveness.

Figure 6B:
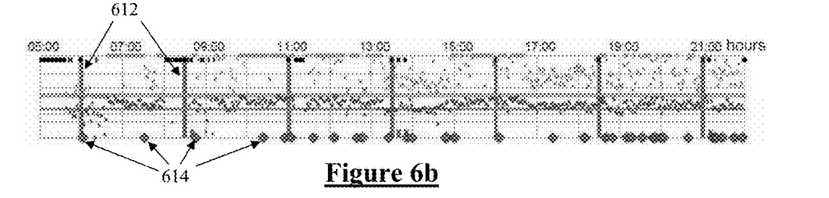

Based on the instructions given, FIG. 6a illustrates a typical patient's response over the course of one day. In particular, FIG. 6a gives an example of the output from one day of wrist-worn data logger recording from a patient who was prescribed 6 doses of levodopa/day. The upper set of dots 606, and the lower set of dots 608, represent the exception that two acknowledgements followed the 06:00 AM reminder. In contrast, another patient's response profile is shown in FIG. 6b. In response to seven reminders (612) in the day shown, the subject in FIG. 6b provided thirty five acknowledgments (614) when only seven were required. This is represented as a Response Ratio (RR), namely the actual number of responses recorded, expressed as a percentage of the number expected. Thus the RR for the patient in FIG. 6a was 116%, whereas the response ratio for the patient in FIG. 6b was 500%. The patient response also includes an automated dyskinesia score (606) and an automated bradykinesia (608) score, each produced repeatedly over the course of the day in accordance with the teaching of International Patent Publication No. WO 2009/149520, each score being shown as a dot or point in the response profile. A greater deviation of the dyskinesia scores above the midline indicates stronger dyskinesia, and a greater deviation of the bradykinesia scores below the midline indicates stronger bradykinesia. It is notable that the subject of FIG. 6b had many more dyskinesia scores at higher levels with many at the upper levels of the graph (e.g. 10:00 am to 11:00 am), as compared to the subject of FIG. 6a.

Figure 6C:
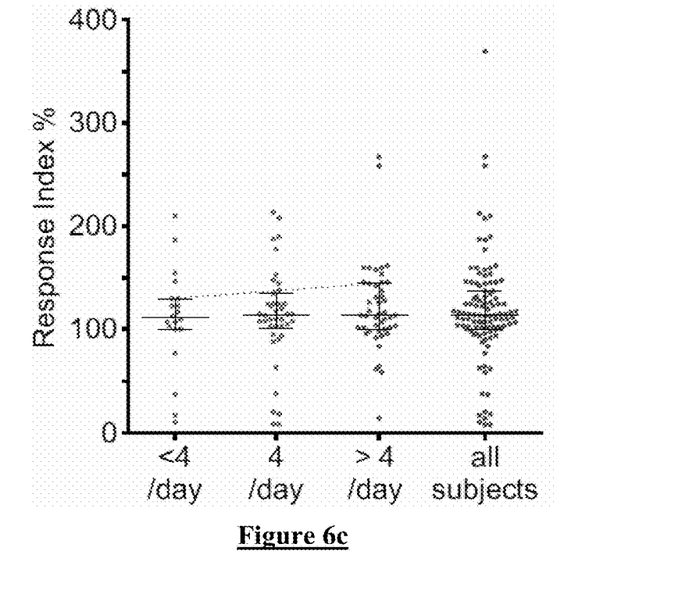
FIG. 6c is a scatterplot of Response Ratio of patients grouped by medication doses.

In this study described here as Example 2, the recording for each patient was taken over 10 days so the RR was calculated for the whole 10 days that the wrist-worn data logger was worn. The median RR in 108 subjects who had worn the wrist-worn data logger in the past 6 months was 116, and the $75^{th}$ percentile was 136. Twenty three percent of patients who took 4 or less doses of levodopa/day had RR scores over the $75^{th}$ percentile, whereas the RR in patients taking 5 or more doses/day was 63 percent (p<0.5 $\chi^2$ test). This indicates that high RRs are more common in patients with wearing off (i.e. more frequent levodopa dosing), as shown in the scatterplot of FIG. 6c.

Figure 6D:
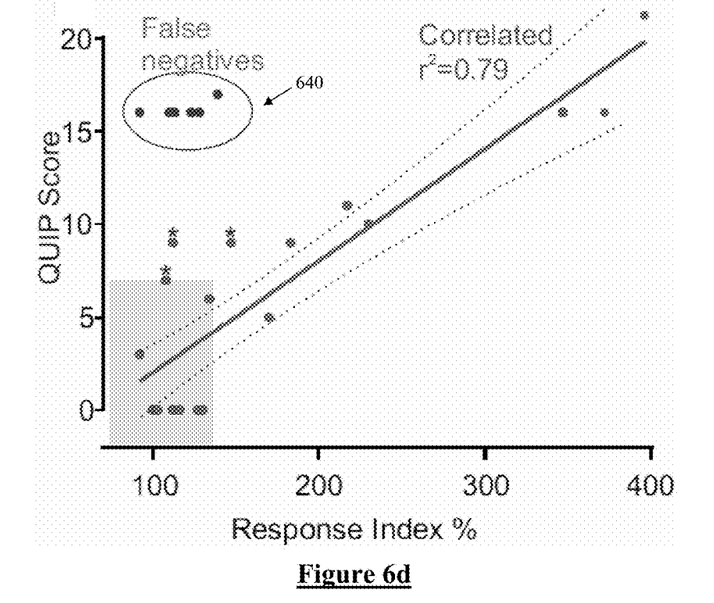
FIG. 6d is a plot of QUIP score against Response Ratio.

The possibility that the increased RR may represent a form of ICB was investigated by examining the relationship between RR and QUIP, BIS/BAS, STAI and Starkstein AS scores in twenty-five subjects. Six subjects were previously identified as having ICBs, but who had not previously worn the wrist-worn data logger. Nineteen subjects were selected by an unblinded assessor from the 108 subjects who had recently worn the wrist-worn data logger because they either had a high RR (>137: n=7) or because their RR was less than 137 (n=12). A second assessor, who was blinded to the selection process, administered the scales and questionnaires and arranged for all subjects to wear a wrist-worn data logger. The QUIP score was plotted against the RR score obtained from the report of the type shown in FIGS. 6a and 6b. FIG. 6D is a plot of the QUIP score (y axis) plotted against the RR (X axis). Two groups are apparent: False Negatives (640: n=6), and a Correlated Group (all other dots: n=19). The grey shaded area represents people whose RR was less than 137% and whose ICB score was 7. In seventeen subjects there was a strong correlation ($r^2$=0.79) with QUIP scores but six were clear outliers and fell into False negative group (540). Thus, the RR was a good predictor of the severity of ICB, as measured by QUIP in 75% of subjects (correlated group) but 25% were false negatives: they had high QUIP scores but a RR within the normal range.

Figure 7A:
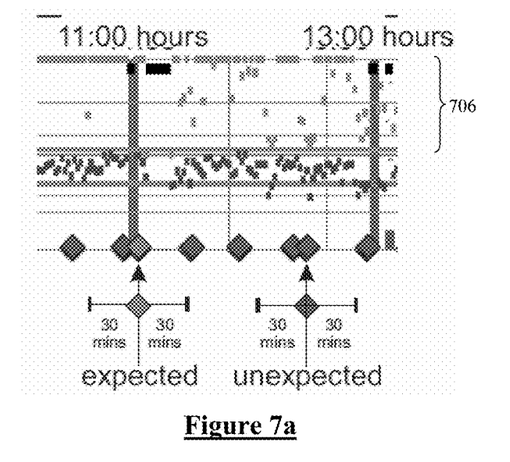
FIG. 7a is a segment of a wrist-worn data logger record from a patient with ICB and high dyskinesia scores.

Because ICBs have been associated with development of dyskinesia, we examined dyskinesia scores in the False Negative Group, a high RR Group (RR>136) and a low RR group (RR<137). First the median of the 2 minute dyskinesia scores 706 from the wrist-worn data logger in the 30 minutes either side of each Response was calculated. FIG. 7A is a segment of the daily wrist-worn data logger record from a person with ICB, with diamond markers showing expected responses and unexpected responses as indicated. Note that in this example, the 2 minute dyskinesia scores 706 are mostly high indicating relatively severe dyskinesia. Furthermore, the median dyskinesia score was calculated in the first valid (expected) response after a reminder and after other (unexpected) responses that led to increased RRs. The median dyskinesia scores of both expected and unexpected responses in the False Negative Group and the low RR subjects were below the median of controls. In comparison, the dyskinesia scores in the 30 minutes either side of expected responses in the correlated group were high, but were significantly higher still in the period surrounding unexpected responses.

Figure 7B:
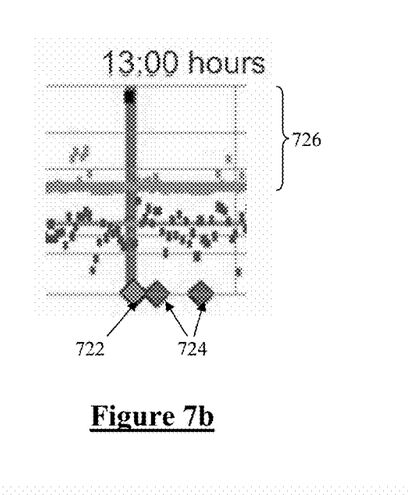
FIG. 7b is a segment of a wrist-worn data logger record from a patient without ICB and having low dyskinesia scores.

In contrast, FIG. 2B shows a segment of the daily wrist-worn data logger record from a person without ICB, showing an expected response (diamond marker 722) and unexpected responses (diamond markers 724). Note that in this example, the 2 minute dyskinesia scores 726 are below the median for controls.

Figure 7C:
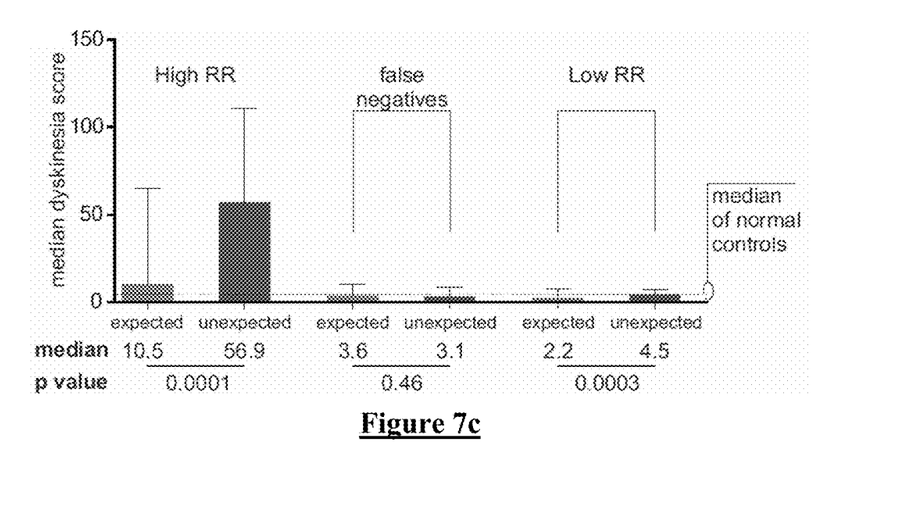
FIG. 7c shows histograms of median dyskinesia score in the 30 minutes either side of expected or unexpected responses, for the High RR group, the False Negative Group and the low RR Group, respectively.

FIG. 7C shows histograms of the median dyskinesia score in the 30 minutes either side of expected and unexpected responses in the High RR group, the False Negative Group and in the low RR Group, respectively. The histogram bars represent the median and $75^{th}$ percentile values for the subjects in each group. The median dyskinesia score in control (i.e. non PD) subjects is shown as a dotted line. Note that median dyskinesia scores of both expected and unexpected responses in the False Negative Group and the low RR subjects were below the median of controls. On the other hand, while the dyskinesia scores associated with expected responses in the correlated group were high, they were significantly higher still in the period surrounding unexpected responses. The P value associated with each expected and unexpected response is shown.

The False Negative Group 640 tended to have higher Starkstein Apathy scores than the Correlated Group (p=0.06 Mann Whitney) and a less significant trend toward higher STAI (p=0.15 Mann Whitney) and lower BIS/BAS scores (p=0.16 Mann Whitney). Taken together this suggests that the False Negative Group are indeed a separate entity who have ICBs without dyskinesia and have higher Apathy but lower impulsivity than might otherwise be expected of subjects with ICBs.

The duration of PD in the High RR group was significantly longer (medians 16 v 10 years: p<0.05 Mann Whitney) and the BDI scores (medians 15 v 7 years: p<0.05 Mann Whitney) significantly higher than the low RR group (Table 2). The values for the False Negative subjects fell between the other two groups and did not reach significance (Table 2). There was a trend for the high RR group to have worse UPDRS, ACE-R, SCOPA COG, STAI and AS scores and to take more LED, but none reached statistical significance (Table 2). The values in the False negative group were in general intermediate between the other two groups. One third of the Low RR group (4 out of 11) were on DA2 receptor agonists whereas 2 out of 8 of the High RR subjects and 5 out of 6 of the False negatives were on DA2 receptor agonists.

The median dyskinesia score from the wrist-worn data logger obtained from 10 days of recording in the time between 9:00 and 18:00 was significantly higher in the high RR group than in the low RR and False Negative groups (P<0.05: Kruskal Wallis) as was the UPDRS IV scores (P<0.05: Kruskal Wallis). The median dyskinesia score in the False Negative Group was intermediate between the Correlated and non ICB groups.

FIG. 6D indicates that the False Negatives are outliers, lying well outside the confidence limits of the other subjects, and the data presented above point to grounds for regarding the outliers as a separate entity 640. In this context it is possible that the three red dots marked by asterisk in FIG. 6d, which fall outside the confidence limits, are incipient members of the False Negative Group 640. Most of the subjects in the study were questioned about the reasons that they used the reminders excessively. Many were unaware that they had responded excessively and those were aware could not provide an explanation. All were adamant that they did not use it to indicate increased consumption of medications. When the False Negative group 640 are excluded, there was high level of agreement between the QUIP and RR Index in detecting ICBs (p=0.0012: Fishers exact and free-marginal kappa value of 0.79).

The study of Example 2 shows that a high RR index is a sensitive test for the presence of ICBs. That is, subjects with a High RR will almost always have ICBs. The question of whether the failure to detect the False Negative Group 640 indicates reduced selectivity or more likely, a separate form of ICBs, is discussed further in the following. Subjects with high RR/QUIP scores in the correlated group had higher median dyskinesia scores over the ten days while wearing the wrist-worn data logger. The finding that the UPDRS IV was higher in this group also reflects the greater sensitivity of continuous objective measurement of dyskinesia with the wrist-worn data logger in evaluating dyskinesia.

The finding that dyskinesia scores are high in the 30 minutes either side of an expected response is consistent with knowledge that ICBs are more likely to occur in the "on" state, in those at risk of ICBs. However, it is illuminating that the dyskinesia scores at the time of unexpected responses are higher still, which raises the possibility that the unexpected responses reflect a disturbance in the reward related processes. It may be that the behaviours examined in this study, consisting of a tactile stimulus followed by ingestion of medications that cause excessively elevated levels of DA in the striatum, lead to enhanced 'learning' of an acknowledgement response. In turn, the Response has taken on a salience similar to that of a cue in a conditioned stimulus in associative learning. It has been demonstrated in some subjects that striatal dopamine may contribute to the attribution of Pavlovian incentive values to cues that signal reward, thus making them valuable in their own right, and so individuals with a propensity to this form of reward learning, where "incentive salience" is assigned to reward cues, are at risk of the cues driving the behaviour. However, where the cue does not carry this incentive salience, striatal dopamine does not play the same central role in the associative learning.

Example 2 thus indicates that the Correlated Group represents a group with abnormally high levels of striatal dopamine, for whom the Response has gained salience in its own right. The elevated RR is a marker for ICBs because it is a marker of the risk of propensity to abnormally assign "incentive salience" to reward cues. Conversely, the False Negative group 640 may represent a different form of ICB, such as a group with prefrontal pathology in which changes occur in the function of frontal circuitry associated with the overvaluing of drug reinforcers, the undervaluing of alternative reinforcers, and deficits in inhibitory control for drug responses, where dopamine may play less of a role.

Thus, in some embodiments, the invention may be applied in conjunction with a dyskinesia score. The dyskinesia score may be generated for example in accordance with the teaching of International Patent Publication No. WO 2009/149520, the content of which is incorporated herein by reference, and in particular the dyskinesia score may be generated as taught at pages 7-10 or pages 16-19 of that disclosure, for example. In such embodiments, the validity of an ICD diagnosis may be improved if resulting from a period in which dyskinesia is also present, as unnecessary additional actuations which occur during dyskinesia are more likely to be a result of ICD. Such embodiments are advantageous in that the same wrist-worn device may be used both to obtain accelerometer data to produce the dyskinesia score, and to provide alarms to the user in accordance with its existing purpose of improving the medication regime, and to gather the actuation rate information to obtain the automated ICD diagnosis. Using the dyskinesia score as an added input, in addition to the actuation data, has been found to improve the discrimination accuracy of the automated ICD diagnosis.

In further embodiments, the ICD diagnosis may further be made responsive to the timeframe in which the actuations of the user occur. In particular, ICD behaviour typically occurs sooner after the wrist-worn device issues the medication reminder than other infrequent and unrelated behaviours. Thus, detected actuations of the button which occur shortly after the reminder may be taken in such embodiments to give a stronger indication of ICD, whereas actuations of the button which do not occur soon after the reminder may be given less weight as being indicative of ICD. The time frame of interest after the reminder may for example be a period of between 5 and 60 minutes after the reminder, and may be in clusters that follow quickly after each other in the following 60 minutes.

The present invention may be particularly applicable to Parkinson's disease patients, as the taking of medication is a rewarding task and so the patient is strongly motivated to comply with instructions around taking medication.

Nevertheless, it is to be appreciated that the present invention may be applied in other applications. For example a reformed smoker may be reminded to apply a nicotine patch as a reward task, and may be instructed to press a button each time they do so to deactivate the reminder. Pressing the button is thus made salient to the reward task. Once again, a response rate which significantly exceeds 100% may be used as a marker of ICD. Alternatively, the actuator may be the lid of a container of cigarettes, whereby opening or closing of the lid is monitored, and is salient to the reward task of smoking.

In another embodiment the present invention may be applied to an impulsive gambler, who may be alerted whenever they have lost a predefined increment of money while gambling, and be required to press a button to deactivate the alert, thus making the pressing of the button salient to the reward task of gambling.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of using an actuator to assess likelihood that an individual has impulse control disorder, the method comprising:
   providing the individual with the actuator, and instructing the individual to actuate the actuator as an acknowledgement of when the individual has taken medication;
   monitoring and recording the actuation of the actuator, wherein the actuator is located on a device that reminds the individual to take medication, wherein the device is configured to remind the individual to take medication when required, and wherein the actuator deactivates the reminder to indicate that the medication has been taken;
   producing, by a processor, an automated diagnosis of the likelihood of impulse control disorder, wherein a greater degree of actuation of the actuator by the individual is taken to indicate a greater likelihood that the individual has impulse control disorder; and
   outputting the automated diagnosis of the likelihood that the individual has impulse control disorder.

2. The method of claim 1 wherein performance of the taking of the medication by the individual is not monitored by actuation of the actuator.

3. The method of claim 1 wherein the actuator is at least one of a button, dial, lever, questionnaire tick-box, and a sensor or input device responsive to a motor response of the individual.

4. The method of claim 1 wherein the device is body-worn.

5. The method of claim 1 wherein the device is located separate from the individual.

6. The method of claim 1 further comprising generating an output that the individual is at-risk of impulse control disorder when the individual actuates the actuator by an amount which is moderately more than expected, and generating an output that the individual has impulse control disorder when the individual actuates the actuator by an amount which is significantly more than expected.

* * * * *

UNITED STATES PATENT AND TRADEMARK OFFICE
CERTIFICATE OF CORRECTION

PATENT NO. : 10,292,635 B2
APPLICATION NO. : 14/771965
DATED : May 21, 2019
INVENTOR(S) : Griffiths et al.

It is certified that error appears in the above-identified patent and that said Letters Patent is hereby corrected as shown below:

On the Title Page

Item (71):
Delete "Global Kinetics Corporation Limited," and insert --Global Kinetics Pty Ltd,--

Item (72):
Delete "Home," and insert --Horne,--

Page 2, Column 2, Item (56), Other Publications, Line 15:
Delete "Presss," and insert --Press,--

Page 2, Column 2, Item (56), Other Publications, Line 24:
Delete "Ameircan" and insert --American--

Page 2, Column 2, Item (56), Other Publications, Line 47:
Delete "Accelometry," and insert --Accelerometry,--

Page 2, Column 2, Item (56), Other Publications, Line 57:
Delete "Asessment," and insert --Assessment,--

Page 2, Column 2, Item (56), Other Publications, Line 60:
Delete "Quanitfication" and insert --Quantification--

Page 2, Column 2, Item (56), Other Publications, Line 64:
Delete "Pateints" and insert --Patients--

Page 3, Column 1, Item (56), Other Publications, Line 28:
Delete "Intesity" and insert --Intensity--

Signed and Sealed this
Twelfth Day of November, 2019

Andrei Iancu
*Director of the United States Patent and Trademark Office*

CERTIFICATE OF CORRECTION (continued)
U.S. Pat. No. 10,292,635 B2

Page 3, Column 1, Item (56), Other Publications, Line 28:
Delete "ande" and insert --and--

Page 3, Column 1, Item (56), Other Publications, Line 49:
Delete "at al.," and insert --et al.,--

Page 3, Column 1, Item (56), Other Publications, Line 55:
Delete "aftger" and insert --after--

Page 3, Column 1, Item (56), Other Publications, Line 60:
Delete "Quanitfy" and insert --Quantify--

Page 3, Column 2, Item (56), Other Publications, Line 11:
Delete "hypokenisia" and insert --hypokinesia--

Page 3, Column 2, Item (56), Other Publications, Line 23:
Delete "Analysisof" and insert --Analysis of--

Page 3, Column 2, Item (56), Other Publications, Line 41:
Delete "Internation" and insert --International--

Page 4, Column 2, Item (56), Other Publications, Line 14:
Delete "Behaviioural" and insert --Behavioural--

Page 4, Column 2, Line 25:
Delete "(Intemational-type)" and insert --(International-type)--